US007003350B2

(12) United States Patent
Denker et al.

(10) Patent No.: US 7,003,350 B2
(45) Date of Patent: *Feb. 21, 2006

(54) INTRAVENOUS CARDIAC PACING SYSTEM WITH WIRELESS POWER SUPPLY

(75) Inventors: Stephen Denker, Mequon, WI (US); Arthur J. Beutler, Greendale, WI (US)

(73) Assignee: Kenergy, Inc., Mequon, WI (US)

( * ) Notice: Subject to any disclaimer, the term of this patent is extended or adjusted under 35 U.S.C. 154(b) by 117 days.

This patent is subject to a terminal disclaimer.

(21) Appl. No.: 10/700,148

(22) Filed: Nov. 3, 2003

(65) Prior Publication Data

US 2005/0096702 A1    May 5, 2005

(51) Int. Cl.
*A61N 1/365* (2006.01)
(52) U.S. Cl. ........................................................ 607/33
(58) Field of Classification Search .............. 607/2–10, 607/30–33, 37, 60, 61, 122, 126; 128/903; 623/1.15
See application file for complete search history.

(56) References Cited

U.S. PATENT DOCUMENTS

| 5,170,802 | A | 12/1992 | Mehra |
| 5,411,535 | A | 5/1995 | Fujii et al. |
| 5,531,779 | A | 7/1996 | Dahl et al. |
| 5,713,939 | A | 2/1998 | Nedungadi et al. |
| 5,739,795 | A | 4/1998 | Chanteau et al. |
| 5,741,316 | A | 4/1998 | Chen et al. |
| 5,814,089 | A | 9/1998 | Stokes et al. |
| 5,954,761 | A | 9/1999 | Machek et al. |
| 5,995,874 | A | 11/1999 | Borza |
| 6,026,818 | A | 2/2000 | Blair et al. |
| 6,067,474 | A | 5/2000 | Schulman et al. |
| 6,138,681 | A | 10/2000 | Chen et al. |
| 6,141,588 | A | 10/2000 | Cox et al. |
| 6,431,175 | B1 | 8/2002 | Penner et al. |
| 6,442,413 | B1 | 8/2002 | Silver |
| 6,445,953 | B1 | 9/2002 | Bulkes et al. |
| 2002/0005719 | A1 | 1/2002 | Gilboa et al. |
| 2002/0026228 | A1 | 2/2002 | Schauerte |
| 2002/0128546 | A1 | 9/2002 | Silver |
| 2002/0183791 | A1 * | 12/2002 | Denker et al. .................. 607/5 |
| 2003/0158584 | A1 * | 8/2003 | Cates et al. .................... 607/2 |

* cited by examiner

*Primary Examiner*—George Manuel
(74) *Attorney, Agent, or Firm*—George E. Haas; Quarles & Brady LLP

(57) ABSTRACT

A cardiac pacemaker includes a power transmitter which periodically transmits a pulse of a radio frequency signal to a vascular electrode-stent that is implanted in a vein or artery of an animal. The vascular electrode-stent employs energy from the radio frequency signal to charge a storage device which serves as an electrical power supply. The vascular electrode-stent also detects a cardiac signal emitted from the sinus node of the heart and responds thereto by applying a pulse of voltage from the storage device to a pair of electrodes implanted in the vascular system of the animal. Application of the voltage pulse to the electrodes stimulates contraction of the heart.

19 Claims, 2 Drawing Sheets

INTRAVENOUS CARDIAC PACING SYSTEM WITH WIRELESS POWER SUPPLY

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of the Invention

The present invention relates to implantable medical devices which deliver energy to heart tissue to stimulate cardiac contractions, and more particularly to such cardiac pacing devices that are implantable in a vein or artery.

2. Description of the Related Art

A remedy for people with slowed or disrupted natural heart activity is to implant a cardiac pacing device which is a small electronic apparatus that stimulates the heart to beat at regular rates.

Typically the pacing device is implanted in the patient's chest and has sensor electrodes that detect electrical impulses associated with in the heart contractions. These sensed impulses are analyzed to determine when irregular cardiac activity occurs, in which event a pulse generator is triggered to produce electrical pulses. Wires carry these pulses to patch-type stimulation electrodes placed adjacent specific cardiac muscles, which when electrically stimulated contract the heart chambers. It is important that the stimulation electrodes be properly located to produce contraction of the heart chambers.

Modern cardiac pacing devices vary the stimulation to adapt the heart rate to the patient's level of activity, thereby mimicking the heart's natural activity. The pulse generator modifies that rate by tracking the activity at the sinus node of the heart or by responding to other sensor signals that indicate body motion or respiration rate.

U.S. Pat. No. 6,445,953 describes a cardiac pacemaker that has a pacing device, which can be located outside the patient, to detect irregular or weak cardiac activity. In that event, the pacing device emits a radio frequency signal, that is received by a circuit mounted on a stent implanted in a vein or artery of the patient's heart. Specifically, the radio frequency signal induces a voltage pulse in an antenna on the stent and that pulse is applied across a pair of electrodes on the stent, thereby stimulating adjacent muscles and contracting the heart. Although this cardiac pacing apparatus offered several advantages over other types of pacemakers, it required placement of sensing electrodes on the patient's chest in order for the external pacing device to detect when the heart requires stimulation.

SUMMARY OF THE INVENTION

A cardiac pacing apparatus is provided to artificially stimulate contractions of a heart in an animal. That apparatus includes a power transmitter which periodically transmits a pulse of a radio frequency signal to a vascular electrode-stent that is implanted preferably in a vein or artery the animal.

The vascular electrode-stent comprises an pickup device, such as a coil of wire for example, for receiving the radio frequency signal and a cardiac signal emitted from the sinus node of the heart. A pacing signal circuit is connected to the pickup device and a pair of electrodes that are in contact with tissue of the animal. The pacing signal circuit has an electrical storage device that is charged by electrical energy from the radio frequency signal. In response to detecting the cardiac signal, the pacing signal circuit applies a stimulation voltage pulse across the pair of electrodes to cause a contraction of the heart.

In a preferred embodiment of the vascular electrode-stent, the pacing signal circuit includes a discriminator and a pulse circuit. The discriminator is connected to the pickup device and controls charging of the electrical storage device in response to detecting a pulse of the radio frequency signal. When the discriminator detects the cardiac signal, a trigger signal is produced, which causes the pulse circuit to apply the stimulation voltage pulse across the pair of electrodes.

DETAILED DESCRIPTION OF THE INVENTION

Figure 1:
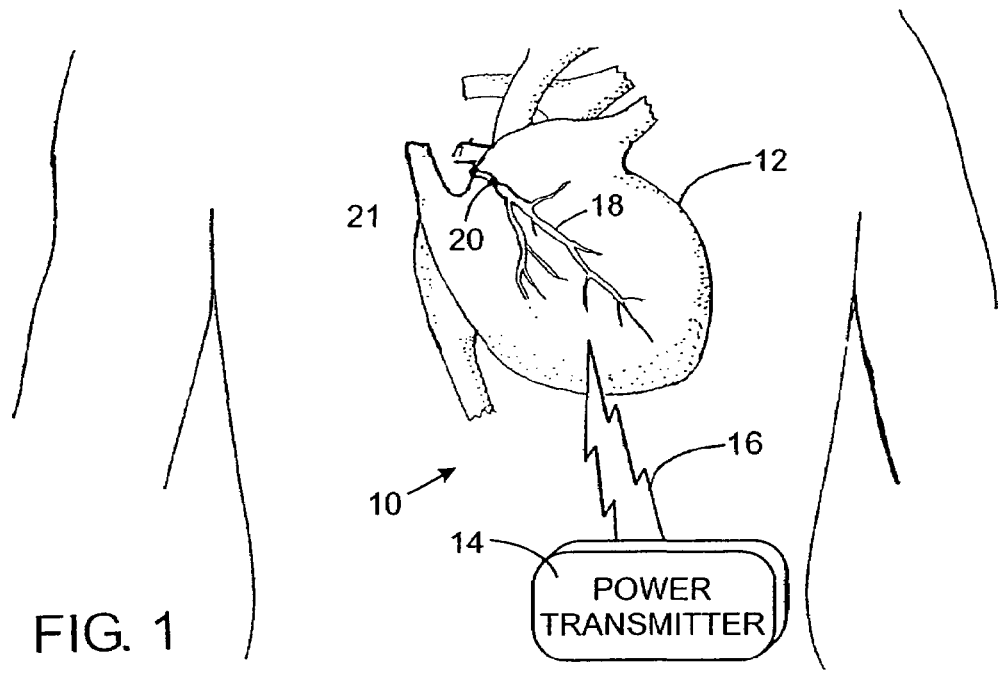
FIG. 1 is a representation of a cardiac pacing apparatus attached to a medical patient.

With initial reference to FIG. 1, a pacing apparatus 10 for electrically stimulating a heart 12 to contract comprises a power transmitter 14 and a vascular electrode-stent 20. The power transmitter 14 preferably is worn outside the patient's body adjacent the chest and emits a radio frequency signal 16 which is received by the vascular electrode-stent 20. Alternatively, the power transmitter 14 may be implanted in the patient. As will be described in greater detail, receipt of radio frequency signal 16 provides electrical power for circuitry on the electrode-stent. The vascular electrode-stent 20 is placed in an artery or vein 18 which carries blood through the heart in close proximity to the sinus node. For example the vascular electrode-stent 20 may be positioned in the _____ artery.

Figure 2:
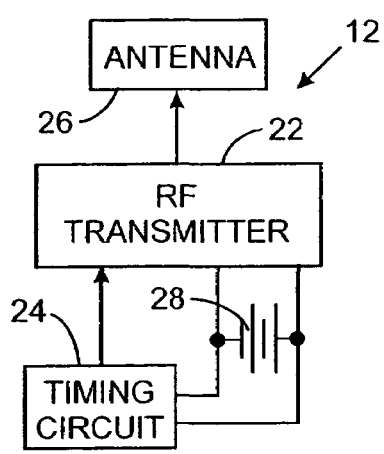
FIG. 2 is a circuit diagram of a power transmitter for the cardiac pacing apparatus.

Referring to FIG. 2, the power transmitter 14 comprises a radio frequency (RF) transmitter 22 connected to a timing circuit 24 and to an antenna 26. Both the RF transmitter 22 and the timing circuit 24 are powered by a battery 28. The timing circuit 24 controls the RF transmitter 22 to emit periodic pulses of the radio frequency signal 16. For example, the pulses have relatively slow rising and falling edges, as shown in FIG. 4A, so that the signal level gradually increases and decreases.

Figure 3:
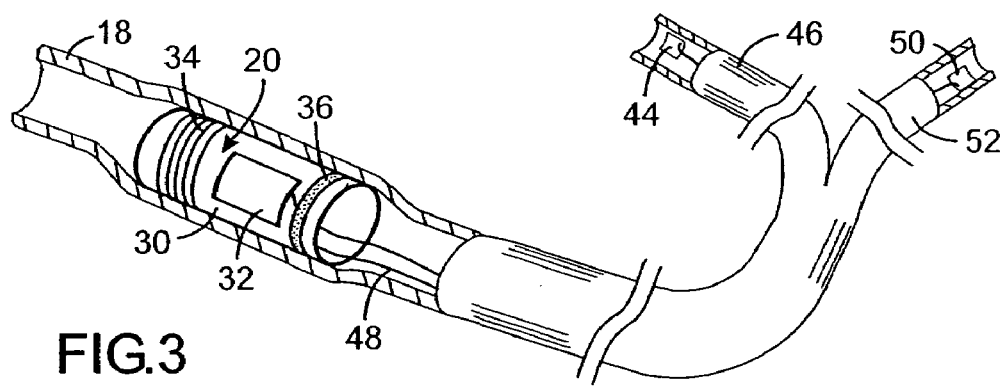
FIG. 3 is an isometric cut-away view of cardiac blood vessels in which a vascular electrode-stent and a second electrode have been implanted.

As illustrated in FIG. 3, the electrode-stent 20 includes a body 30 similar to well-known expandable vascular stents that are employed to enlarge a restricted vein or artery. Such vascular stents have a generally tubular shape that initially is collapsed to a relatively small diameter enabling them to pass freely through blood vessels of a patient. The procedure for implanting the electrode-stent 20 is similar to that used for conventional vascular stents. For example, a balloon at the end of a standard catheter is inserted into the vascular electrode-stent 20 in a collapsed configuration. That assembly is inserted through an incision in a vein or artery near the skin of a patient and pushed through the vascular system to the appropriate location proximate to the sinus node of the heart 12. The balloon of the catheter then is inflated to expand the vascular electrode-stent 20, thereby slightly enlarging the blood vessel 18 which embeds the electrode-stent in the wall of the vein or artery. The balloon is deflated, the catheter is removed from the patient, and the incision is closed. Alternatively, a self-expanding stent may be utilized as the body 30. The slight enlargement of the blood vessel 18 and the tubular design of the stent's body 30 allows blood to flow relatively unimpeded through the vascular electrode-stent 20.

Figure 4:
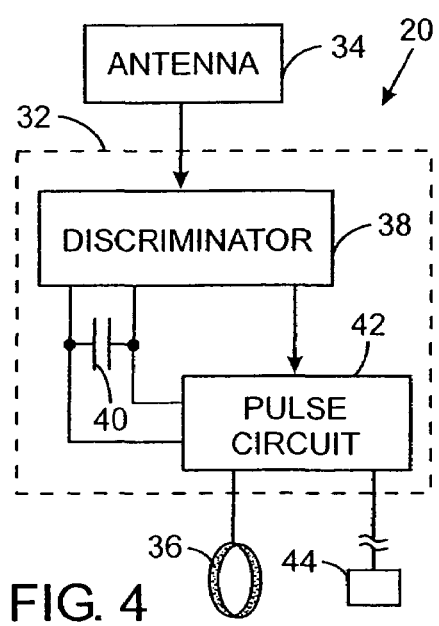
FIG. 4 is a block diagram of an electrical circuit on the vascular electrode-stent shown in FIG. 2.

With reference to FIGS. 3 and 4, the vascular electrode-stent 20 has a pacing signal circuit 32 and a pickup device 34 in the form of a wire coil wound circumferentially around the body 30. A first electrode 36 in the form of a ring encircles the body. The pacing signal circuit 32 includes a pulse discriminator 38 connected to the pickup device 34. As will be described, the pulse discriminator 38 distinguishes between electrical pulses induced in the pickup device by electrical events at the sinus node of the heart and by the RF signal 16 from the power transmitter 14. That distinguishing is based on the shape of the respective signal waveform and the pulses of those waveforms as illustrated in FIG. 4A for the RF signal 16 and in FIG. 4B for the cardiac signal from the sinus node. The RF signal has relatively long duration pulses with gradually rising and falling edges. In contrast, the electrical pulses of the cardiac signal are very short duration and rise and fall quickly. The pulse discriminator 38 also is able to detect when both types of pulses coincide in time.

Whenever an RF signal pulse is detected, the pulse discriminator 38 uses the energy of that signal to charge a storage capacitor 40 which supplies electrical power to the circuitry on the vascular electrode-stent 20. Other types of electrical storage devices may be employed. The radio frequency signal supplies power to the vascular electrode-stent, and unlike prior wireless pacemakers does not trigger cardiac stimulation.

The sinus node of the heart 12 emits an electrical cardiac signal which causes contraction of the heart chambers. The cardiac signal travels from cell to cell in paths through the heart to muscles which contract the atria. This signal also propagates along another path until reaching the atrioventricular (AV) node, which is a cluster of cells situated in the center of the heart between the atria and ventricles. The atrioventricular node serves as a gate that slows the electrical current before the cardiac signal is permitted to pass to the ventricles. This delay ensures that the atria have a chance to fully contract before the ventricles are stimulated.

Figure 5A:
FIGS. 5A, B, and C are waveform diagrams of three electrical signals in the cardiac pacing apparatus.
Figure 5B:
Figure 5C:

Due to the placement of the vascular electrode-stent 20 in proximity to the sinus node, emission of the cardiac signal also induces an electric current pulse in the pickup device, or coil, 34 of the vascular electrode-stent 20, as depicted in FIG. 5B. The pulse discriminator 38 recognizes the rapid rise time of this pulse as being produced by the cardiac signal, as compared to a RF signal pulse shown in FIG. 5A. When a cardiac signal pulse is detected, the pulse discriminator 38 issues a trigger signal to a pulse circuit 42. The pulse circuit 42 is similar to circuits used in previous cardiac pacing devices which generate voltage pulses for stimulating a contraction of the heart, as shown in FIG. 5C. Specifically, upon being triggered the pulse circuit 42 uses the charge on the capacitor 40 to produce a voltage pulse that is applied between the first electrode 36, that extends around the stent body, and a second electrode 44, which is remote from the vascular electrode-stent 20.

As shown in FIG. 3, the second electrode 44 is secured to the wall of a blood vessel 46 in another section of the heart and is connected to the pulse circuit 42 by a thin insulated wire 48 extending through the blood vessels. The relatively small size of the second electrode 44 allows it to be placed into a significantly smaller blood vessel 46 than the vascular electrode-stent 20. As a result, the second electrode 44 can be placed is a greater variety of locations in the cardiac vascular system and in close proximity to the muscles that contract the desired portion of the heart 12.

Depending upon whether the second electrode 44 is placed to stimulate contraction of an atrium or a ventricle, the pulse circuit 42 delays a predefined amount of time after receiving the trigger signal from the pulse discriminator 38 before applying the voltage pulse to the first and second electrodes. Therefore, timing of muscle stimulation corresponds to that which occurs with respect to naturally induced contraction of the atrium or ventricle. The duration of that delay is programmed into the pulse circuit 42 by the surgeon upon implantation and is a function of the location of the second electrode.

In another version of the vascular electrode-stent 20, one or more additional electrodes, such as a third electrode 50, can be implanted in other cardiac blood vessels 52 to stimulate further sections of the heart. In this case, individual voltage pulses can be applied between the first electrode 36 and each of the additional electrodes 44 and 50 to separately stimulate contraction of those other sections of the heart. A stimulation pulse also may be applied between the second and third electrodes 44 and 50, without using the first electrode 36.

The foregoing description was primarily directed to preferred embodiments of the invention. Even though some attention was given to various alternatives within the scope of the invention, it is anticipated that one skilled in the art will likely realize additional alternatives that are now apparent from disclosure of embodiments of the invention. Accordingly, the scope of the invention should be determined from the following claims and not limited by the above disclosure.

We claim:

1. A cardiac pacing apparatus, for artificially stimulating contractions in a heart of an animal, comprising:
   a power transmitter which periodically transmits a pulse of a radio frequency signal;
   a first electrode and a second electrode for implantation in the animal; and
   a vascular electrode-stent for implantation in a blood vessel of the animal and comprising a pickup device for receiving the radio frequency signal and a cardiac signal emitted from a sinus node of the heart, and a pacing signal circuit connected to the pickup device and having an electrical storage device, wherein the pacing signal circuit charges the electrical storage device with electrical energy from the radio frequency signal and in response to detecting the cardiac signal determines when stimulation is required and applies a stimulation voltage pulse across the first electrode and the second electrode to cause a contraction of the heart.

2. The apparatus as recited in claim 1 wherein the first electrode is mounted on the vascular electrode-stent.

3. The apparatus as recited in claim 1 wherein the electrical storage device is a capacitor.

4. The apparatus as recited in claim 1 wherein the pickup device comprises a coil.

5. The apparatus as recited in claim 1 wherein the pacing signal circuit comprises:
   a discriminator connected to the pickup device, and charging the electrical storage device in response to detecting a pulse of the radio frequency signal, and producing a trigger signal in response to detecting the cardiac signal; and
   a pulse circuit connected to the discriminator and the electrical storage device, and applying the stimulation voltage pulse across the first electrode and the second electrode in response to the trigger signal.

6. The apparatus as recited in claim 5 wherein the discriminator distinguishes between the radio frequency signal from the power transmitter and the cardiac signal emitted from the sinus node based on differences in their signal waveforms.

7. The apparatus as recited in claim 6 wherein each pulse of the radio frequency signal from the power transmitter has a leading edge which is longer in duration than a leading edge of the cardiac signal emitted from the sinus node.

8. The apparatus as recited in claim 1 wherein the pulses of the radio frequency signal from the power transmitter and pulses of the cardiac signal emitted from the sinus node are asynchronous.

9. The apparatus as recited in claim 1 further comprising a third electrode for implantation in the animal and connected to the vascular electrode-stent, wherein the pacing signal circuit applies a voltage pulse to the third electrode.

10. A cardiac pacing apparatus, for artificially stimulating contractions in a heart of an animal, comprising:
    a power transmitter which periodically transmits a pulse of a radio frequency signal;
    a vascular electrode-stent for implantation in a blood vessel of the animal and comprising a body, a pacing signal circuit on the body, a pickup coil for receiving the radio frequency signal and a cardiac signal emitted from a sinus node of the heart, and a first electrode mounted to the body; and
    a second electrode for implantation in a blood vessel of the animal;
    the pacing signal circuit comprises an electrical storage device, a discriminator connected to the pickup coil and charging the electrical storage device in response to detecting a pulse of the radio frequency signal and producing a trigger signal in response to detecting the cardiac signal, and a pulse circuit connected to the discriminator and the electrical storage device and applying a stimulation voltage pulse across the first electrode and the second electrode to cause a contraction of the heart.

11. The apparatus as recited in claim 10 wherein the body is expandable within the blood vessel from a first cross-sectional size to a second cross-sectional size.

12. The apparatus as recited in claim 10 wherein the first electrode is a conductive ring that encircles the body of the vascular electrode-stent.

13. The apparatus as recited in claim 10 wherein the electrical storage device is a capacitor.

14. The apparatus as recited in claim 10 wherein the discriminator distinguishes between the radio frequency signal from the power transmitter and the cardiac signal emitted from the sinus node based on differences in their signal waveforms.

15. The apparatus as recited in claim 14 wherein each pulse of the radio frequency signal from the power transmitter has a leading edge which is longer in duration than a leading edge of the cardiac signal emitted from the sinus node.

16. The apparatus as recited in claim 10 wherein the pulses of the radio frequency signal from the power transmitter and pulses of the cardiac signal emitted from the sinus node are asynchronous.

17. The apparatus as recited in claim 10 further comprising a third electrode for implantation into a blood vessel of the animal and connected to the pacing signal circuit, wherein the pulse circuit applies a voltage pulse between the first and third electrodes.

18. The apparatus as recited in claim 10 further comprising a third electrode for implantation into a blood vessel of the animal and connected to the vascular electrode-stent, wherein the pacing signal circuit applies a voltage pulse between the second and third electrodes.

19. A method for stimulating contractions of a heart of an animal, the method comprising:
    implanting a vascular electrode-stent into a blood vessel at a first location in the animal, the vascular electrode-stent comprising a pacing signal circuit and a pickup device and a first electrode both of connected to the pacing signal circuit that has an electrical storage device;
    implanting a second electrode into a blood vessel at a second location in the animal, wherein the second electrode is connected to the pacing signal circuit of the vascular electrode-stent;
    transmitting a radio frequency signal to the vascular electrode-stent;
    charging the electrical storage device with electrical energy received by the pacing signal circuit from the radio frequency signal;
    the pacing signal circuit detecting emission of a cardiac signal from a sinus node of the heart; and
    the pacing signal circuit responding to detecting emission of the cardiac signal by determining when stimulation is required and applying voltage, from the electrical storage device, across the first and second electrodes to stimulate contraction of the heart.

* * * * *